United States Patent [19]

Inoue et al.

[11] Patent Number: 5,087,426
[45] Date of Patent: Feb. 11, 1992

[54] OZONE DEODORIZER FOR REFRIGERATORS

[75] Inventors: Yoshitaka Inoue, Neyagawa; Teruo Sato, Yahata; Tutomu Hiromi, Kyoto, all of Japan

[73] Assignees: Matsushita Electric Industrial Co., Ltd., Osaka; Yushin Engineering Corporation, Kyoto, both of Japan

[21] Appl. No.: 518,359

[22] Filed: May 3, 1990

[30] Foreign Application Priority Data

May 9, 1989 [JP] Japan .................. 1-115352

[51] Int. Cl.$^5$ ............................................. A61L 9/00
[52] U.S. Cl. ...................... 422/123; 422/28; 422/29; 422/116; 422/186.07; 422/186.16; 422/305; 55/150
[58] Field of Search ............. 422/28, 29, 32, 116, 422/123, 186.07, 186.15, 186.16, 305; 320/13; 55/150

[56] References Cited

U.S. PATENT DOCUMENTS

| | | | |
|---|---|---|---|
| 3,421,836 | 1/1969 | Sundin et al. | 422/32 |
| 4,349,511 | 9/1982 | Owen | 55/150 |
| 4,666,679 | 5/1987 | Masuda et al. | 422/186.07 |
| 4,690,803 | 9/1987 | Hirth | 422/186.07 |
| 4,707,338 | 11/1987 | Spector | 422/124 |
| 4,736,416 | 4/1988 | Weinert | 422/28 |
| 4,743,275 | 5/1988 | Flanagan | 55/150 |
| 4,833,583 | 5/1989 | Petitimbert | 422/186.16 |
| 4,970,056 | 11/1990 | Wooten et al. | 422/186.07 |

FOREIGN PATENT DOCUMENTS 3230365 9/1984 Fed. Rep. of Germany ........................ 422/186.07

Primary Examiner—Robert J. Warden
Assistant Examiner—Theresa A. Trembley
Attorney, Agent, or Firm—Panitch Schwarze Jacobs & Nadel

[57] ABSTRACT

An ozone deodorizing device for use in refrigerators, in which ozone is intermittently generated under action of a timer by use of a creepage discharger to avoid consumption of the battery, the discharge quantity is equalized by use of a pulse generator varying its pulse width to compensate for the reduction of battery power.

6 Claims, 6 Drawing Sheets

OZONE DEODORIZER FOR REFRIGERATORS

BACKGROUND OF THE INVENTION

1. Field of the Invention

The present invention relates to an ozone deodorizing device for use in refrigerators and more particularly to a cordless ozone deodorizing device operable on a battery.

2. Description of the Prior Art

Ozone deodorizing devices operable on a commercial power source are known and used. These ozone deodorizing devices have cords connected to a power source. However, the cord becomes an obstacle when used in a confined space like refrigerators.

The known ozone deodorizing devices operable on a commercial power source use fine ceramic ozone-generating dischargers, which comprise a dielectric layer between a high voltage electrode and a ground electrode, the layer having a thickness of 0.3 to 1.0 mm. The application of a high voltage to the discharger generates highly concentrated ozone.

The known ozone deodorizing apparatus mentioned above has the following disadvantages:

The consumption of electricity is high. The cord structure makes it difficult to place the ozone deodorizing device in a confined space such as a refrigerator.

To solve this problem, cordless ozone deodorizing devices using a battery have been proposed. However, in return for the cordless structure, a voltage stabilizer circuit is required to compensate for the discharge of the battery and maintain constant voltage to secure even corona discharge. Alternatively, a feedback is applied to the driving section by detecting the amount of corona discharge so as to equalize the amount of corona discharge.

SUMMARY OF THE INVENTION

The ozone deodorizing device of the present invention, which overcomes the above-discussed and numerous other disadvantages and deficiencies of the prior art, comprises a battery power source, a timer for controlling the generation of ozone intermittently, a pulse generator for narrowing pulse widths when the battery voltage is high, and widening them when the battery voltage is low, and a creepage discharger for generating ozone, the creepage discharger comprising a thin dielectric layer disposed between a high-voltage electrode and a ground electrode.

According to another aspect of the present invention, the ozone deodorizing device comprises a battery power source, a timer for controlling the generation of ozone intermittently, a pulse generator for narrowing pulse widths when the battery voltage is high, and widening them when the battery voltage is low, and a creepage discharger for generating ozone, the creepage discharger comprising a ground electrode, a thin dielectric layer, a high-voltage electrode and outermost layer laid in this order on a ceramic substrate, wherein the dielectric layer is disposed between the ground electrode and the high-voltage electrode and has a thickness of 45 $\mu$m to 100 $\mu$m.

In a preferred embodiment, the outermost layer and the dielectric layer are made of the same material.

In another preferred embodiment, the ratio of the thickness of the dielectric layer to that of the outermost layer is about 3 to 5:1.

In a further preferred embodiment, the dielectric layer and the outermost layer are made of any of the substances of alumina, nitride glass, heat-resistant glass, ruby and sapphire.

In a still further embodiment, the ground electrode is band-shaped, the high-voltage electrodes located in opposition to the ground electrode and the dielectric layer, the high-voltage electrode being ribbon-shaped with a smaller thickness than that of the ground electrode.

In a preferred embodiment, the ground electrode is band-shaped, and the high-voltage electrodes located in opposition to the ground electrode through the dielectric layer comprise a stem and a round head, wherein the ratio of the area of the stem to that of the round head is about 2:1.

The basic principle underlying the present invention will be described:

The output of the pulse generator used has a short pulse width when the battery voltage is high thereby reducing power consumption. This prolongs the life of the battery. As the battery voltage drops, the pulse width increases thereby ensuring that the desired amount of ozone is generated.

In the fine ceramic creepage discharger used in the present invention which employs a battery for the power source, a dielectric layer between a high voltage electrode and a ground electrode is only 45 $\mu$m to 100 $\mu$m thick, thus making it possible to generate only low levels of ozone, and by making the ratio of the thickness of an outermost layer to that of the dielectric layer 1:3 to 5, ozone is easily generated at low voltages.

The creepage discharger has a high-voltage electrode of a matchstick shape with a stem and a round head wherein the ratio of the surface area of the round head to that of the stem is 1:2 so that a uniform electric field distribution is achieved.

A creepage discharger of the type described above using fine ceramic is considered as an equivalent to a capacitor, and a discharge occurs when the energy stored in the capacitor is released. Where the voltage impressed on the creepage discharger is V and the equivalent capacitance of the discharger is C, the level of energy W stored in the discharger is given by $$W = \frac{1}{2} CV^2 \quad (1)$$

The equivalent capacitance C of the discharge element is given by $$C = \epsilon_0 \epsilon_s \frac{S}{t} \quad (2)$$

where $\epsilon_0 = 8.85 \times 10^{-12}$ (dielectric constant in a vacuum); $\epsilon_s$ is the specific dielectric constant of the dielectric layer where t is the gap between electrodes, that is, the thickness of the dielectric layer, and S is the surface area of the electrode.

From equations (1) and (2) above, the following equation (3) is obtained.

$$W = \frac{1}{2} \epsilon_0 \epsilon_s \frac{S}{t} V^2 \quad (3)$$

The insulation breakdown voltage Vr is given by the relational expression $Vr = A \cdot t^n$ ($n = 0.3$ to $1.0$), where A is a constant of the insulating material.

In the creepage discharge, the dielectric layer breaks at a relatively low voltage if it is thin. In the discharge occurring at low voltage the breakdown thickness of air becomes small; that is, the amount of discharge is decreased. From the relationship of equation (2), a smaller discharge level and a lower insulation breakdown voltage can be satisfied as conditions by making the thickness t of the dielectric layer thinner, lowering the insulation breakdown voltage Vr, and lowering the discharge energy W by making the electrode surface area S smaller. The specific dielectric constant es can also be lowered, but experiments show that this unfavorably affects the efficiency of ozone generation. Thus there is a lower limit for lowering the specific dielectric constant.

The strength of the electric field at the beginning of discharge in a gas varies, that is, in air it is 33 kV/cm, in oxygen it is 27 kV/cm and in nitrogen it is 35.4 kV/cm. As the discharge voltage lowers, nitrogen oxides are reduced at lower discharge voltages.

Thus, the invention described herein makes possible the objectives of (1) providing a cordless ozone deodorizing device operable on a battery, (2) providing an ozone deodorizing device capable of reducing the current consumption and equalizing fluctuations in the discharge level due to the decrease in battery voltage, (3) providing an ozone deodorizing device capable of being used in a confined or sealed space, without paying attention to the connection to the power source, and (4) providing an ozone deodorizing device capable of prolonging the life of the battery by reducing the consumption of electricity.

BRIEF DESCRIPTION OF THE DRAWINGS

This invention may be better understood and its numerous objects and advantages will become apparent to those skilled in the art by reference to the accompanying drawings as follows.

DETAILED DESCRIPTION OF THE INVENTION

Figure 1:
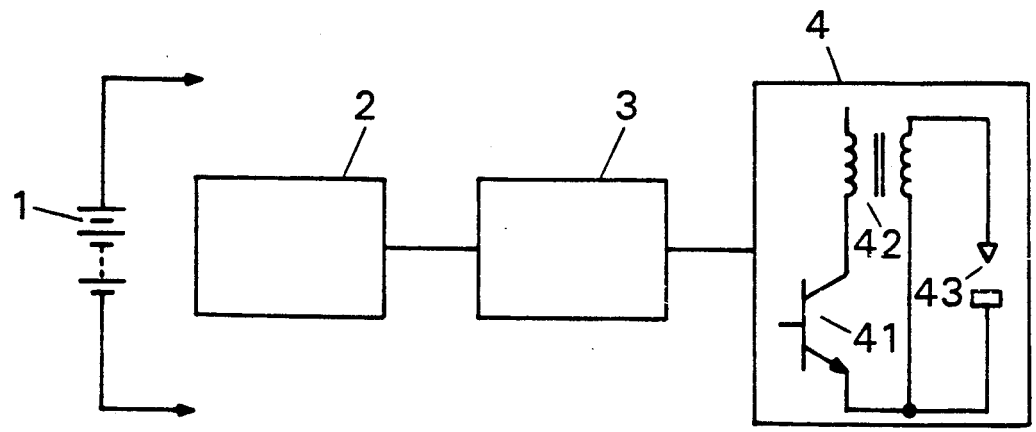
FIG. 1 is a diagram showing an electric circuit used in an ozone deodorizing device according to the present invention.

In FIG. 1, which shows a diagram of an ozone generating circuit, there are provided a battery 1, a timer 2, and a pulse generator 3 which operates only when the output of the timer 2 is on at a high level. The output pulse widths of the pulse generator vary with the voltage of the battery 1: when the voltage of the battery is high, the pulse width becomes narrow, and when the voltage is low, the pulse width becomes wide. There is also provided an ozone generating section 4 which comprises a transistor 41, a pulse transformer 42 and an ozone generator 43. An optimum ozone concentration in the ozone deodorizing device is two to three times that of the odor, and it is necessary to decompose excess ozone in the exhaust by means of a catalyst. If the ozone concentration is excessively high, an increased amount of catalyst is required to decompose it, and this increases the cost. However, when the ozone generation results from corona discharge in air, it is difficult to maintain moderate corona discharge for a sufficient period of time. In cases where a relatively weak deodorizing effect is sufficient such as in a refrigerator, it is recommendable to generate strong discharges at short time intervals so as to achieve a desired concentration of ozone through the repeated discharges. As described below, the ozone generating circuit used in the present invention is controlled so that ozone will be intermittently generated by differentiation of rectangular waves. The duty factor of ozone generation in this embodiment is approximately 0.03.

Figure 2:
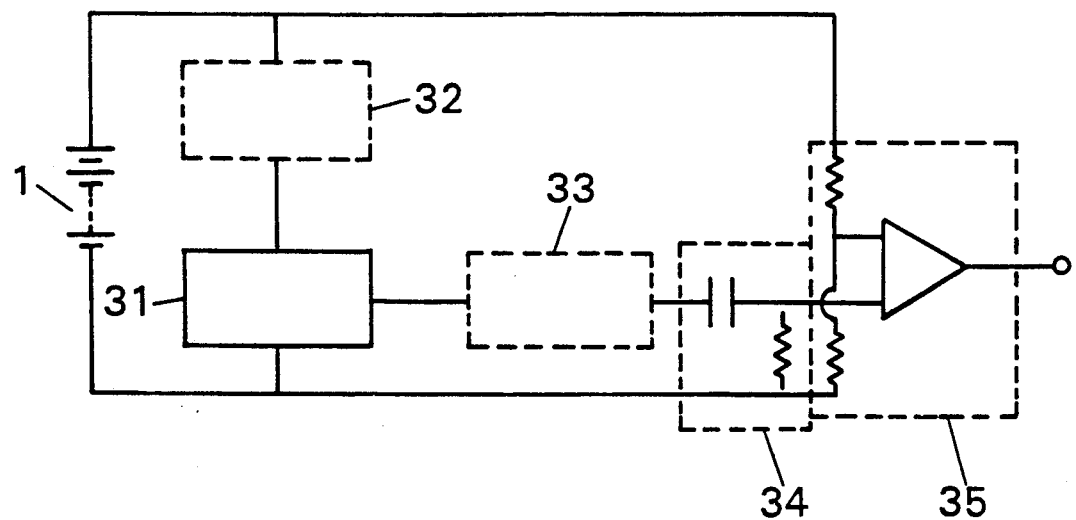
FIG. 2 is a diagram showing an electric circuit of a pulse generator used in the ozone deodorizing device of the present invention.
Figure 3:
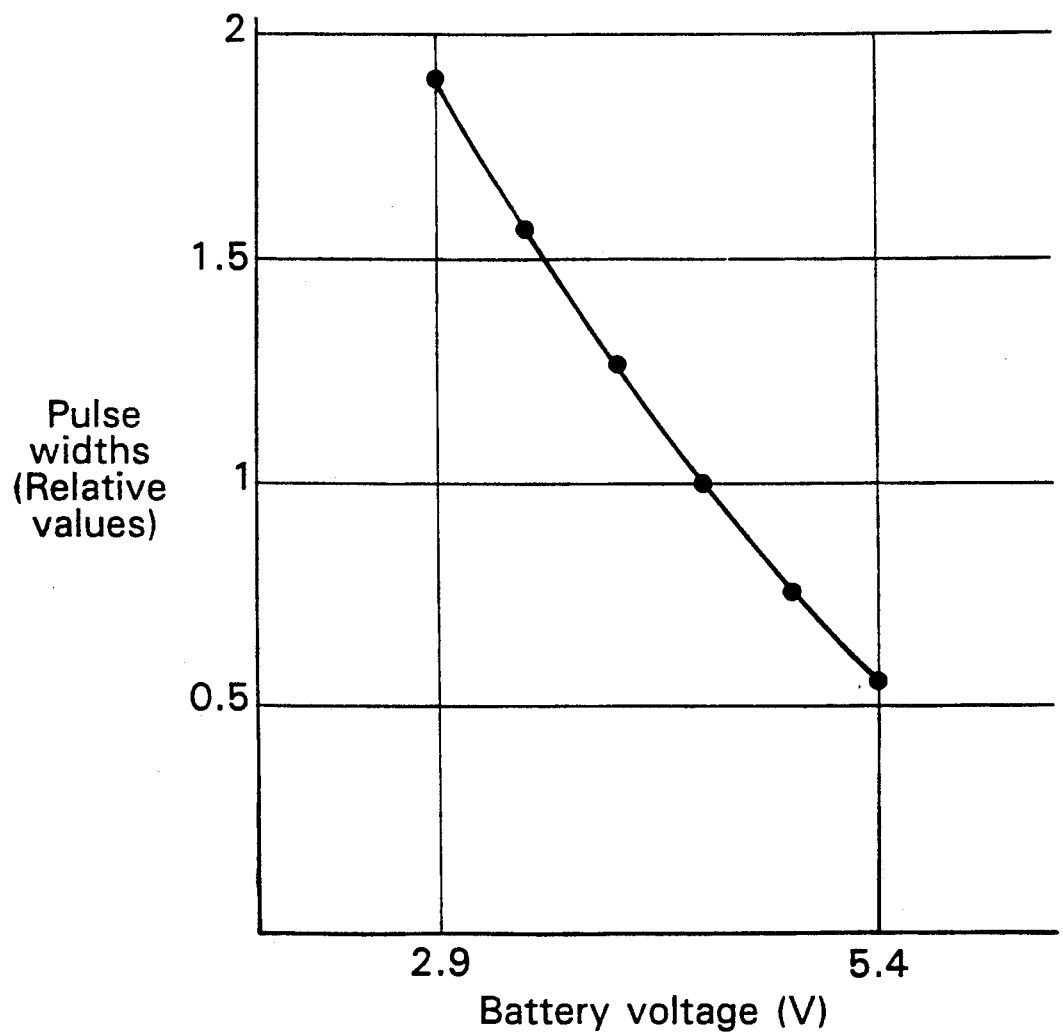
FIG. 3 is a graph showing one example of pulse width modulation characteristics of the pulse generator.

Referring to FIG. 2, which is a diagram showing an electric circuit in the pulse generator 3, an example of the operation of the ozone deodorizing device will be described:

There is provided a rectangular wave oscillator 31, the amplitude of whose rectangular wave output is maintained constant by connecting it to the battery via a constant voltage circuit 32 or attaching an amplitude control circuit 33 to the output of the oscillator 31. After a pulse edge of a constant width is differentiated, for example, by a differentiating circuit 34, which is composed of a capacitor and a resistance, it is supplied to a comparator 35 where it is compared with a reference voltage which is proportional to the source voltage. FIG. 3 shows a graph of the logical values of a sample output characteristic of the pulse generator 3 where the source voltage is 2.9–5.4 V and the rectangular wave amplitude is 3.5 V. As is evident from the FIG. 3, when the battery voltage is high, the pulse width becomes narrow, and the pulse transformer 42 driven by this pulse receives large power energy for a short period of time. When the battery voltage is lower, the pulse width becomes wider, and it receives small power energy for a longer period of time. In this way the changes in the battery voltage are compensated. The pulse duty factor when the power source voltage is 4.4 V is approximately 0.03.

In this case, since the threshold voltage of a C-MOS gate used as the comparator 35 is virtually proportional to the source voltage, various types of C-MOS gates can be used. Since the timer 2 and the pulse generator 3 are preferably composed of C-MOS ICs which consume less electricity, the consumption of the battery 1 is negligible while ozone is not generated.

Figure 4:
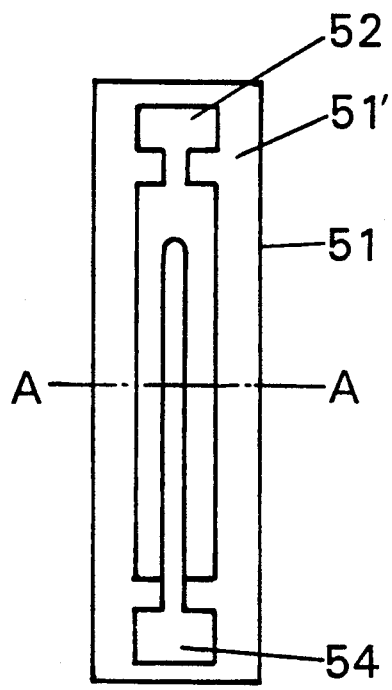
FIG. 4 is a top view of the creepage discharger used in the embodiment of the present invention.
Figure 5:
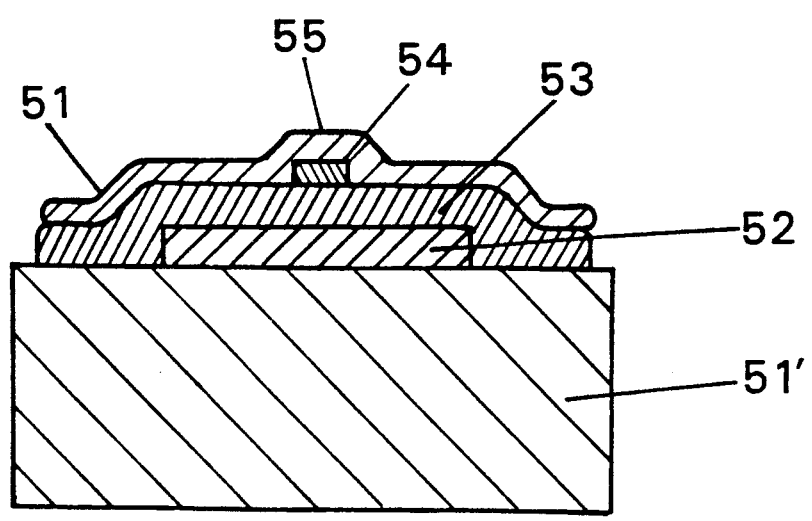
FIG. 5 is a cross-sectional view on an enlarged scale showing the creepage discharger.

Referring to FIG. 4, the creepage discharger will be described in detail:

The creepage discharger 51 has a ceramic substrate 51' of 0.5–1.0 mm thick. The reference numerals 52 and 54 denote a ground electrode and a high voltage electrode, respectively. FIG. 5 is a cross section along line A-A' of the creepage discharger 51, and the thickness of each layer is exaggerated to show contrasts therebetween more clearly.

As shown in FIG. 5, the creepage discharger 51 is formed by laminating, from the bottom upward, the band-like ground electrode 52, a dielectric layer 53, and the ribbon-like high-voltage electrode 54 which is narrower than the ground electrode 52, and an outermost layer 55 on the fine ceramic substrate 51'. It has been found that in the fine ceramic creepage discharger 51 in the present invention, the ratio of the thickness t1 of the dielectric layer 53 to the thickness t2 of the outermost layer 55 has a marked influence on the discharge characteristic. The results are shown below.

When $t1/t2 < 2$, the dielectric layer breaks down.
When $t1/t2 = 2-3$, the discharge range is narrow.
When $t1/t2 = 3-5$, the discharge range is widest.

When the thickness of the outermost layer 55 is uneven, the discharge fatally concentrates in the uneven parts. To avoid this, a tolerance is set to be 15 $\mu$m to 20 $\mu$m. From this tolerance, the thickness of the dielectric layer 53 will amount to be 45 $\mu$m to 100 $\mu$m. The outermost layer 55 and the dielectric layer 53 can be made either of the same or different material. The material includes alumina, nitride glass, heat-resistant glass, ruby, sapphire, etc.

In proportion with an increase in the specific dielectric constant $\epsilon s$, the discharge voltage becomes lower and the creepage discharger 51 is easily excited, but when the property, durability and cost of the material used are taken into consideration, it is preferred that fine ceramic having a specific dielectric constant of 9.5 and a grain size (pre-sintering) of 7 $\mu$m or less, is used.

Figure 6:
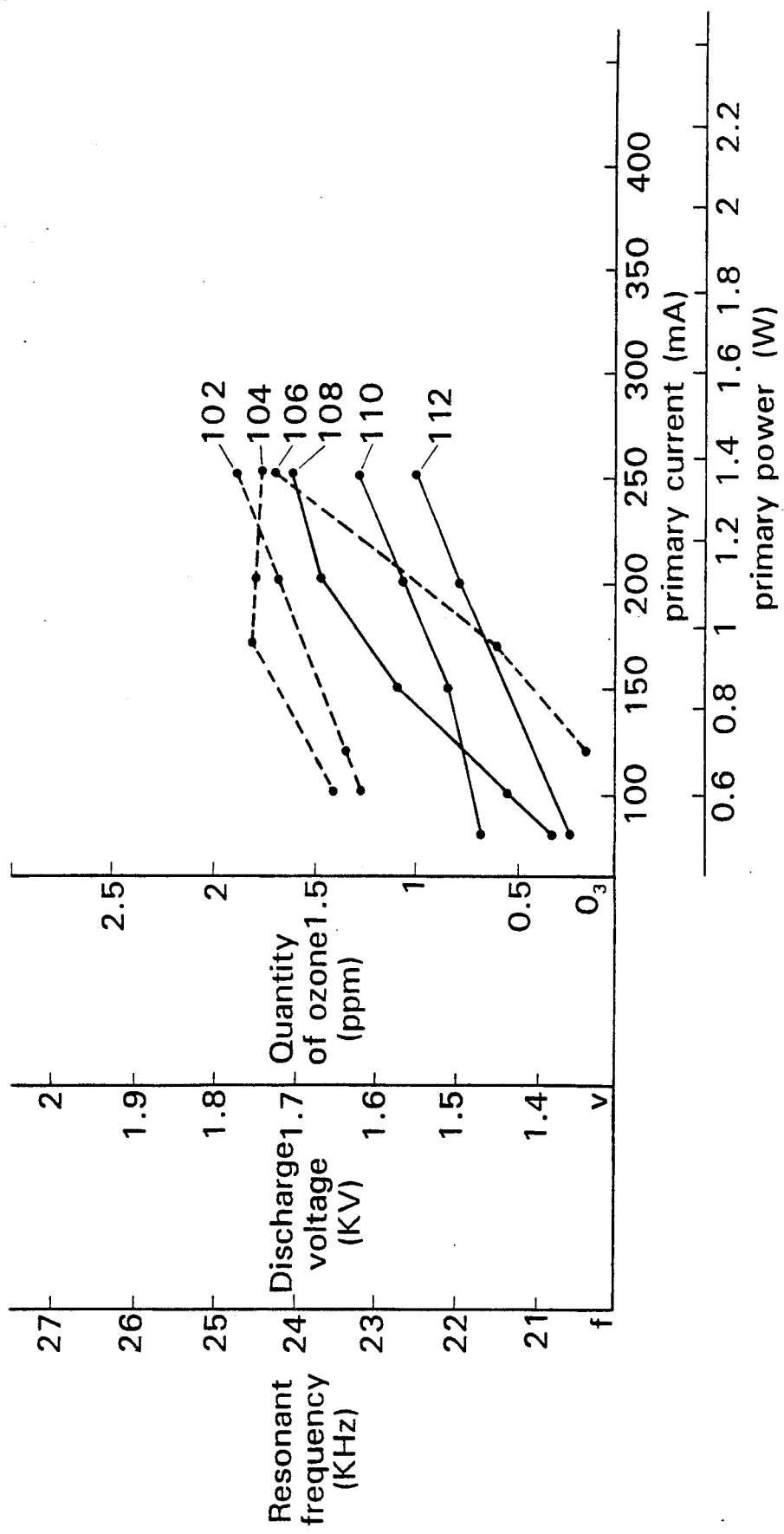
FIG. 6 shows graphs depicting the characteristics of the creepage discharger.

FIG. 6 shows the characteristics of the creepage dischargers having dielectric layers of 60 $\mu$m and 120 $\mu$m. As can be seen from FIG. 6, the level W of ozone generated by the discharger with the 60 $\mu$m-thick dielectric layer, indicated by the solid line, is clearly superior to that of the discharger with the 120 $\mu$m-thick dielectric thickness, indicated by dotted lines, when the primary power is relatively small.

The characteristics of the creepage dischargers were determined at a temperature of 18° C. and a relative humidity of 50%. The flow rate of air was 300 liters per minute. When the amount of air is 300 liter/min, 1 ppm of ozone concentration is expressed in terms of the amount of ozone generated as follows: 38.5 mg/H. This means that when the flow rate of air is 300 liters per minute, 38.5 mg of ozone is generated per 1 ppm in an hour. Dotted line 102 indicates the resonant frequency of a discharger having a dielectric layer of 120 $\mu$m and an outermost layer of 25 $\mu$m. Dotted line 104 indicates the discharge voltage for a discharger having a dielectric layer of 120 $\mu$m and an outermost layer of 25 82 m. Dotted line 106 indicates the generation of ozone for a discharger having a dielectic layer of 120 $\mu$m and an outermost layer of 25 $\mu$m. Solid line 108 indicates the generation of ozone for a discharger having a dielectric layer of 60 $\mu$m and an outermost layer of 20 $\mu$m. Solid line 110 indicates the resonant frequency of a discharger having a dielectic layer of 60 $\mu$m and an outermost layer of 20 $\mu$m. Solid line 112 indicates the discharge voltage of a discharger having a dielectic layer of 60 $\mu$m and an outermost layer of 20 $\mu$m.

Figure 7:
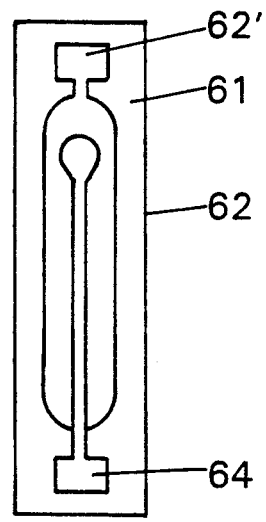
FIG. 7 is a top view showing a modified version of the creepage discharger.

Referring to FIG. 7, another example of the creepage discharger will be described:

The modified creepage discharger 62 is different from the first-mentioned creepage discharger 51 in that the high-voltage electrode 64 is shaped like a matchstick. Likewise in this embodiment the ozone level becomes lower as the capacitance C becomes smaller. On the other hand, the efficiency of generating ozone tends to reduce depending upon the ratio of the capacitance C to the secondary free capacitance of the transformer 42 which drives the creepage discharger 62. To avoid this problem, experiments were conducted. As a result, the high-voltage electrode 64 is shaped like a matchstick, having a width of 0.8 mm and a length of 30 mm and having a round portion at the top end of the stem. The ratio of the area of the stem to that of the round portion is 2 to 1 so as to achieve the uniform electric field distribution and effect the stable discharge in a relatively low concentration and on low power consumption. The capacitance was 30 PF and the resonance frequency when the above drive circuit was used was 20 kHz.

Figure 8:
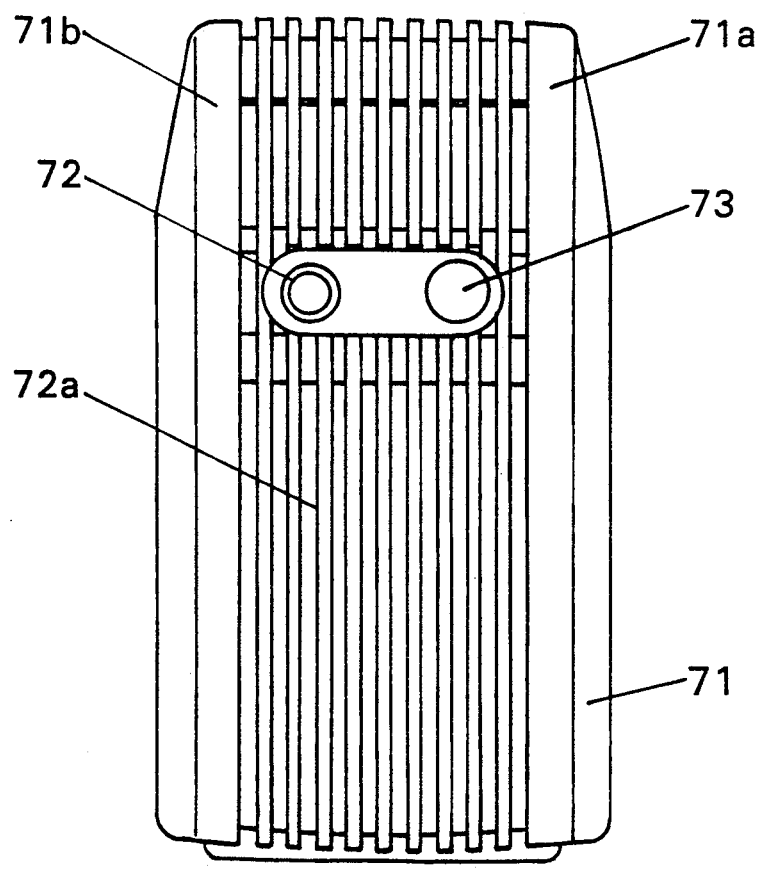
FIG. 8 is a front view showing the outward appearance of the ozone deodorizing device according to the present invention.
Figure 9:
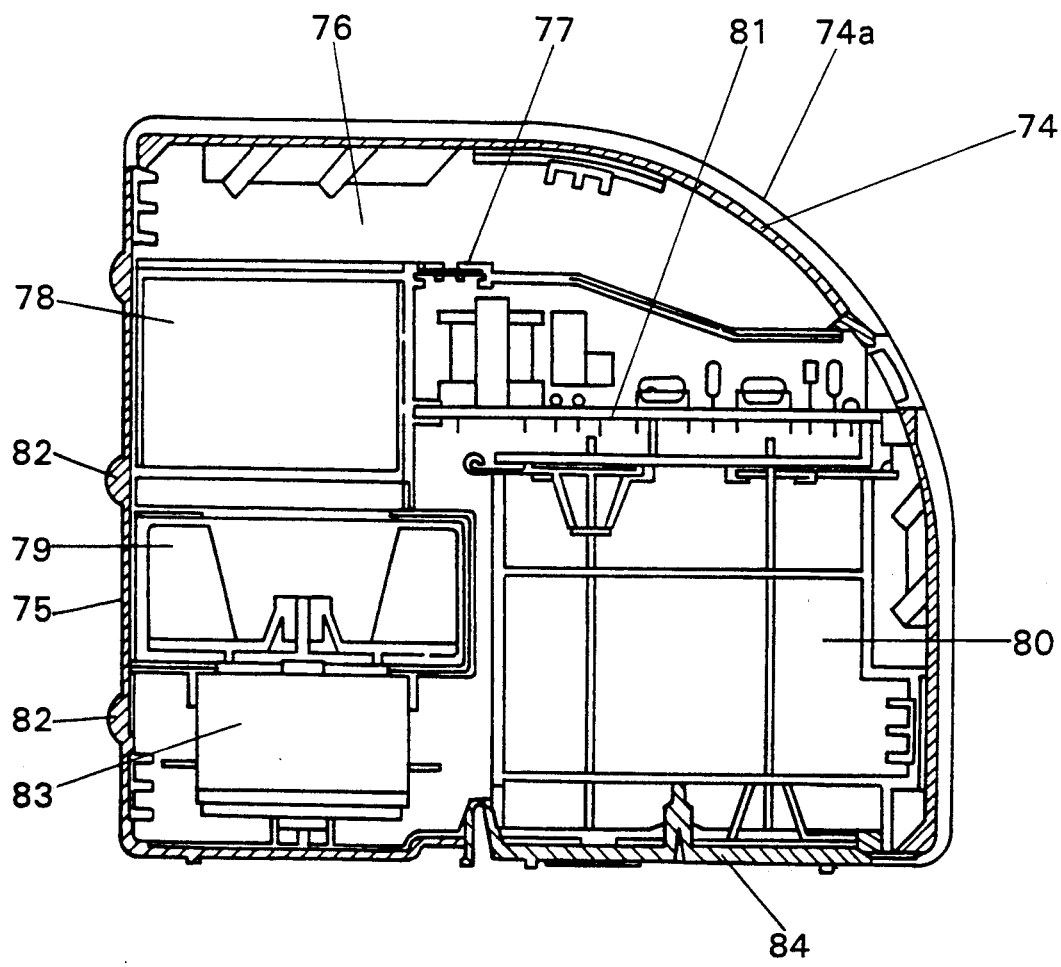
FIG. 9 is a cross-sectional view showing the ozone deodorizing device of FIG. 8.

In referring to FIGS. 8 and 9, the ozone deodorizing device will be described:

The illustrated ozone deodorizing device includes a creepage discharger 77 for generating ozone. The creepage discharger 77 has a casing 71 which consists of halved parts 71a and 71b. The reference numeral 72 denotes a display lamp disposed on a cover 72a. The display lamp 72 lights when the device is operating with the timer on. The operator can observe it. The reference numeral 73 denotes a button for immediately starting the deodorizing device. By pressing the button 73 the second timer is forced into operation, and the deodorizing device is put into operation for a longer period of time than the period of time when the first timer is kept on. Thus the odorant is quickly expelled out of the refrigerator. The reference numeral 74 denotes an intake port which is disposed flush with a portion 74a of the cover 72a. Air is introduced through an intake port 74 and directed to an exhaust port 75 by way of a passage 76. Ozone is generated by a creepage discharger 77, which is situated at such a high place in the passage 76 from the bottom of the intake port 74 or exhaust port 75 so as to avoid water droplets accumulating on the creepage discharger 77. After the substrate of the creepage discharger 77 is fitted in a groove produced in either of the halved parts 71a or 71b, it is held by the other halved part. The reference numeral 78 denotes a honeycomb-shaped catalyst which decomposes odorant and reduces the remaining ozone to oxygen. The reference numeral 79 denotes a fan which induces air through the intake port 74 and expels it through the exhaust port 75. The battery is housed in a case 80. The reference numeral 82 denotes projecting spacers whereby the exhaust port 75 is prevented from being closed by a structure (not shown) such as an inside wall of the refrigerator. The intermittent generation of ozone is effected by a control circuit 81. The fan 79 is driven by a motor 83. The battery is loaded and unloaded by opening a lid 84.

As is evident from the foregoing description, the ozone deodorizing device according to the present invention employs a battery for a power source, and can discharge at a relatively low voltage such as 1700 VP-P or less which is much lower than under the prior art. The safety and reliability of the creepage discharger are enhanced, and the electro-magnetic interference is minimized to a negligible degree. The intermittent generation of ozone minimizes the average power consumption of the battery. The life of the battery is prolonged. Since fluctuations in the battery voltage are compensated by control of the pulse width, the constant ozone concentration is maintained over the entire life of the battery.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An ozone deodorizing device for use in refrigerators, the deodorizing device comprising a battery power source, a timer for controlling the generation of ozone intermittently, a pulse generator for narrowing pulse widths when the battery voltage is high, and widening them when the battery voltage is low, and a creepage discharger for generating ozone, the creepage discharger comprising a ground electrode, a thin dielectric layer, a high-voltage electrode and outermost layer laid in this order on a ceramic substrate, wherein the dielectric layer is disposed between the ground electrode and the high-voltage electrode and has a thickness of 45 µm to 100 µm.

2. An ozone deodorizing device according to claim 1, wherein the outermost layer and the dielectric layer are made of the same material.

3. An ozone deodorizing device according to claim 1, wherein the ratio of the thickness of the dielectric layer to that of the outermost layer is about 3 to 5:1.

4. An ozone deodorizing device according to claim 2, wherein the dielectric layer and the outermost layer are made of any of the substances of alumina, nitride glass, heat-resistant glass, ruby and sapphire.

5. An ozone deodorizing device according to claim 1, wherein the ground electrode is band-shaped, the high-voltage electrodes located in opposition to the ground electrode and the dieletric layer, the high-voltage electrode being ribbon-shaped with a smaller thickness than that of the ground electrode.

6. An ozone deodorizing device according to claim 1, wherein the ground electrode is band-shaped, and the high-voltage electrodes located in opposition to the ground electrode through the dielectric layer comprises a stem and a round head, wherein the ratio of the area of the stem to that of the round head is about 2:1.

* * * * *